United States Patent
Wellen et al.

(10) Patent No.: US 8,876,707 B2
(45) Date of Patent: Nov. 4, 2014

(54) HAND-HELD EAR VACUUM WITH CAMERA AND VIDEO DISPLAY

(76) Inventors: Alexander Wellen, Atlanta, GA (US); J. Gordon Vap, Chevy Chase, MD (US)

(*) Notice: Subject to any disclaimer, the term of this patent is extended or adjusted under 35 U.S.C. 154(b) by 347 days.

(21) Appl. No.: 13/224,914

(22) Filed: Sep. 2, 2011

(65) Prior Publication Data
US 2012/0059224 A1 Mar. 8, 2012

Related U.S. Application Data

(60) Provisional application No. 61/379,868, filed on Sep. 3, 2010.

(51) Int. Cl.
*A61B 1/267* (2006.01)
*A61B 1/227* (2006.01)

(52) U.S. Cl.
CPC .................................. *A61B 1/2275* (2013.01)
USPC ............................................ 600/200; 600/199

(58) Field of Classification Search
USPC ........................... 600/184, 185, 199, 200, 162
See application file for complete search history.

(56) References Cited

U.S. PATENT DOCUMENTS

| | | | |
|---|---|---|---|
| 2,943,184 A | 6/1960 | Christopherson | |
| 5,239,984 A | 8/1993 | Cane et al. | 128/9 |
| 5,363,839 A | 11/1994 | Lankford | 128/9 |
| 5,501,652 A | 3/1996 | Woods | 600/200 |
| 5,527,261 A | 6/1996 | Monroe et al. | 600/109 |
| 5,658,235 A * | 8/1997 | Priest et al. | 600/112 |
| 5,879,289 A | 3/1999 | Yarush et al. | 600/179 |
| 5,885,214 A | 3/1999 | Monroe et al. | 600/407 |
| 5,916,150 A * | 6/1999 | Sillman | 600/184 |
| 5,919,130 A * | 7/1999 | Monroe et al. | 600/200 |
| 6,001,059 A * | 12/1999 | Elliott | 600/184 |
| 6,059,803 A | 5/2000 | Spilman | 606/162 |
| 6,186,944 B1 | 2/2001 | Tsai | 600/200 |
| 6,361,489 B1 | 3/2002 | Tsai | 600/109 |
| 6,406,484 B1 * | 6/2002 | Lang | 606/162 |
| 6,432,046 B1 | 8/2002 | Yarush et al. | 600/179 |
| 6,554,765 B1 | 4/2003 | Yarush et al. | 600/132 |
| 6,569,090 B1 | 5/2003 | Mezzoli et al. | 600/200 |
| 6,626,825 B2 | 9/2003 | Tsai | 600/109 |
| 6,692,432 B1 | 2/2004 | Yarush et al. | 600/179 |
| 6,699,178 B1 | 3/2004 | Koda | 600/104 |
| D494,672 S | 8/2004 | Wang | D24/108 |
| 6,923,760 B2 | 8/2005 | Koda et al. | 600/200 |

(Continued)

FOREIGN PATENT DOCUMENTS

JP 08-173382 7/1996

*Primary Examiner* — Matthew Lawson
*Assistant Examiner* — Si Ming Lee
(74) *Attorney, Agent, or Firm* — Winston & Strawn LLP (57) ABSTRACT

An ear speculum that includes a body having an ear-contacting tip with an opening; a light providing member; a viewing member; and a vacuum intake port, wherein the members and intake port are provided within the ear speculum with the vacuum intake port occupying a larger portion of the of the cross-sectional area of the ear speculum opening than the light providing or viewing members to facilitate removal of material from an ear canal. Also, an otoscope that includes a head; an ear speculum as described herein in operative association with the head; an image detector in image communication with the viewing member; a suction source in vacuum communication with the vacuum intake port; and a light source in illumination communication with the light providing member. Also, a system and method for removing material or debris from an ear canal using the otoscope described herein.

16 Claims, 4 Drawing Sheets

(56) References Cited

U.S. PATENT DOCUMENTS

| | | | |
|---|---|---|---|
| 6,991,638 B2 | 1/2006 | Wang | 606/162 |
| 7,137,948 B2 | 11/2006 | Tsai | 600/109 |
| 8,062,216 B2 * | 11/2011 | Raghuprasad | 600/200 |
| 2002/0038076 A1 * | 3/2002 | Sheehan et al. | 600/200 |
| 2003/0097142 A1 | 5/2003 | Wang | 606/162 |
| 2008/0183125 A1 * | 7/2008 | Issa | 604/26 |

* cited by examiner

HAND-HELD EAR VACUUM WITH CAMERA AND VIDEO DISPLAY

This application claims the benefit of provisional application 61/379,868 filed Sep. 3, 2010, the entire content of which is expressly incorporated herein by reference thereto.

FIELD OF THE INVENTION

The present invention relates to a device that enables an individual to look inside his or her ear canal and easily, quickly, and safely remove earwax, water, drainage, and other debris without the need of a medical doctor.

BACKGROUND OF THE INVENTION

People want an easy and effective way to remove earwax (cerumen), moisture, dead skin, dirt, small microorganisms, and other residue from their ears. A recent study found that despite the introduction of consumer-based 'Do-It-Yourself' earwax removal kits, "there is currently no simple, safe and effective method of self-removal of earwax." (See Leong/Aldern 2005 study). The most common methods are ineffective, messy, brute-force approaches that pose many potential risks, mishaps, and side effects including dizziness, otitis externa ("swimmer's ear"), pain, vertigo, tinnitus, abrasion with bleeding, infection, and perforation of the eardrum.

Cotton swabs are equally ineffective at removing wax and only push the cerumen further into the ear canal. The impaction of the cerumen against the eardrum can cause infection, irritation, pain, and perforation of the eardrum. Home remedies like ear candling is also strongly discouraged by medical practitioners.

Most of the current earwax removal kits on the market include an agent to soften the wax, followed by an irrigation method to loosen and flush out the wax. Different types of methods (i.e., cerumenolysis) are used to soften and rinse out the ear. The type of solutions used in some commercial and consumer products include warm water, hypertonic seawater, hypoallergenic solutions, carbamide peroxide 6.5, glycerin, sodium bicarbonate and glycerin, mineral oil, olive oil, vinegar, alcohol, docusate, and basic saline. If some of the solution remains in the ear canal, it may cause a severe otitis externa that requires medical treatment.

The ear is then irrigated using water or other mixture listed above by a syringe or rubber bulb. In some cases a syringe is preferred over a bulb to avoid inserting the device too far inside the ear canal and causing damage to the eardrum. A syringe will shoot a straighter stream of fluid as well. To limit messiness, an ear basin is used to collect the wax and irrigating solution. To avoid dizziness, warm water irrigation is preferred to the use of cold water. The most common problems reported with any irrigation method include otitis externa ("swimmer's ear"), pain, vertigo, tinnitus, and perforation of the eardrum.

Alternatively, some consumers use a few drops of a solution that evaporates water in one's ear canal and relieves water clogging, discomfort, or the sensation of fullness or hearing impairment. Drops, however, may become trapped behind the wax in the ear canal or cause extreme dryness. Evaporation drops are not effective in removing earwax and other non-fluids.

Ear picks to dig out or loosen earwax also pose dangers to the ear canal and eardrum and are far inferior to what is used by general medical practitioners.

Moreover, there are currently no effective consumer ear vacuums on the market. A recent study found that among the few devices available, none of them were constructed in such a way to created a strong enough vacuum to remove a significant level of wax or water, or to alleviate any discomfort (Leong/Aldern 2005). There are also ear vacuum devices on the market designed to clean hearing aids, but these products do not extract wax or contaminants from the actual ear canal. To date, the only effective ear vacuums are expensive medical devices used by trained practitioners.

Then there are the ear dryers that are designed to dry moisture contained in the ear canal or on the surface of the eardrum, but they are not an effective means of removing earwax or other foreign objects.

U.S. Pat. No. 5,879,289 (Hand-held portable endoscopic camera) describes a device that combines a lens, light source, and video camera in a portable single hand-held housing. The hand-held portable endoscopic camera with display means allows a user to see the interior of the ear canal of a patient, but another person must operate this device. This device is also not necessarily designed for cleaning the ear canal and it does not contain any safety features. It does not disclose any mechanism for removing contaminants from the ear canal. Also, a person cannot self-inspect his or her ear canal using this device because the display is attached to the hand-held body.

U.S. Pat. No. 5,916,150 (Speculum for simultaneously viewing and removing obstructions) discloses a speculum device that allows the user to simultaneously view the ear canal and remove obstructions from the ear canal. This device, however, is a manual device for a medical professional and present deficiencies both as to the viewing and removal of ear wax. Likewise, Japanese Patent No. 8-173382 (Inspecting and cleaning tool for earhole inside) discloses a tool that uses a fiberscope for the inspection of the interior of the ear canal while simultaneously using suction to remove ear wax from the ear canal, but this device does not have an easy-to-manipulate wand. In the Japanese patent, the wax must travel from the inspecting tool via a hose to the base. There reference is also deficient as to the viewing of the person's ear canal and requires the vacuum and lighting means to be located separately from the inspecting tool.

U.S. Pat. No. 5,919,130 (Video otoscope) discloses a video otoscope that displays video images of the interior of the ear on a display means and also has a port to which insufflating air (positive or negative pressure) can be applied "to stimulate the tympanic membrane." This device, however, does not provide for the removal of ear wax but instead includes a port for insufflations so that air can be introduced to stimulate the membrane (or equalize/unblock the Eustachian tube).

None of the products or methods described above allow the user to see adequately inside his or her own ear canal or for that matter another person's ear canal, and effectively, safely and conveniently remove residue and debris from one's own ear. Accordingly, the only way presently available to remove ear wax residue is frequent visits with a trained medical practitioner equipped to use conventional mechanical methods including a curette or Jobson-Horne probe and microsuctioning.

SUMMARY OF THE INVENTION

The present invention relates to a device for allowing a user to observe the interior of their own ear canal on a display, while using suction to extract material such as cerumen, dirt and other debris, as well as water or other fluids.

In particular, the invention relates to an ear speculum comprising a body having an ear-contacting tip with an opening; a light providing member; a viewing member; and a vacuum intake port, wherein the members and intake port are provided within the ear speculum with the vacuum intake port occupying a larger portion of the of the cross-sectional area of the ear speculum opening than the light providing or viewing members to facilitate removal of material from an ear canal.

Advantageously, the light providing member comprises optical fibers; the viewing member comprises a lens; and the vacuum intake port occupies at least 50% of the cross-sectional area of the ear-contacting tip opening.

The invention also relates to an otoscope comprising a head; an ear speculum as described herein in operative association with the head; an image detector in image communication with the viewing member; a suction source in vacuum communication with the vacuum intake port; and a light source in illumination communication with the light providing member.

Advantageously, the otoscope includes a collection chamber in vacuum communication with both the suction source and vacuum intake port, wherein the vacuum intake port is in vacuum communication with the suction source through the collection chamber, with the head configured and dimensioned to house the suction source and collection chamber. Also, the collection chamber is preferably configured and dimensioned such that material suctioned through the vacuum intake port from an ear becomes trapped within the collection chamber before reaching the vacuum source. It is also preferred for the otoscope to include a display for presenting an image obtained by the viewing member; optical components for adjusting the view obtained by the viewing member; a power source operatively connected to the suction source, light source, image detector and display; and controls for adjusting the suction source, light source, optical components and display.

In a particularly useful arrangement, the otoscope further comprises a base connected to and in communication with the head, wherein the base is configured and dimensioned to house the suction source, the monitor and the power source, and the suction source is in vacuum communication with the vacuum intake port through the collection chamber. Also, the optical components generally include a wide angle lens or a zoom lens.

Preferably, the light providing member, the viewing member and the vacuum intake port are arranged concentrically within the ear-contacting tip, and the vacuum port occupies at least 70% of the cross-sectional area of the ear-contacting tip opening, and the viewing member is positioned at the center of the ear-contacting tip. The viewing member and light providing member are generally arranged adjacent and parallel within the ear-contacting tip.

The invention further relates to a system for removing material from an ear canal, comprising an otoscope having a head; an ear speculum as described herein, wherein the proximal end of the ear speculum is in operative association with the head, and there is an opening at the distal end of the ear-contacting tip; a vacuum intake port within the ear-contacting tip; a suction source in vacuum communication with the vacuum intake port, wherein the suction is sufficient to remove any observed material from the ear canal; a light providing member within the ear-contacting tip; a viewing member within the ear-contacting tip; a collection chamber in vacuum communication with both the suction source and vacuum intake port, wherein the vacuum intake port is in vacuum communication with the suction source through the collection chamber; a light source in illumination communication with the light providing member; optics that can obtain and transfer an image of the ear canal to a camera; a base connected to and in communication with the otoscope; a display within the base that presents the image obtained by the camera; a power source within the base electrically connected to the suction source, light source and display; and controls for adjusting the suction, illumination and display.

Another embodiment of the invention relates to a method of extracting debris from an ear canal which comprises providing an otoscope as described herein; inserting the ear-contacting tip into a user's ear canal; observing the interior of the user's ear canal on a display; turning on a suction source to generate a vacuum; vacuuming debris from the user's ear canal while viewing the ear canal on a display; and trapping debris vacuumed from the user's ear canal. As noted herein, the debris is advantageously collected in a collection chamber in the head of the otoscope.

BRIEF DESCRIPTION OF THE DRAWINGS

Further details of the invention become apparent upon review of the following detailed description taken in conjunction with the appended drawing figures wherein.

DETAILED DESCRIPTION OF THE INVENTION

A user with no special or medical training can inspect and remove wax from his or her own ear canal using this device, or the procedure can be performed by another individual who also does not need to possess any special medical training. The device will be of quality construction that doctors with any specialty training could use in their offices. This device could replace the need for the operating microscope and free standing suction machine.

This device employs a higher level of suction than the few consumer ear vacuums now available. Depending upon the specific design of the device, vacuum in the range of 650 to 750 mm Hg can be used. Lower vacuum can be used when the suction device is provided in the head of the device, while slightly greater vacuum can be used when the collection chamber is located remotely from the device. Given the advancement of portable, consumer products, the level of suction for this device is on par with or approaches the level of microsuctioning device used by physicians without subjecting the user's hearing to unnecessary decibel levels.

The invention includes six primary components: (1) a video camera or other image detector, (2) associated optics having fixed magnification or an adjustable zoom (e.g., wide angle lens), (3) a light source and light-providing member, (4) a small, powerful suction or vacuum source coupled to a vacuum collection chamber, (5) a compact monitor or video display, and (6) a power source. These components should be small enough to make the device portable. This is the first device to combine these components in a way to enable an individual to identify and simultaneously remove earwax and residual matter with an unmatched level of precision and safety.

The preferred embodiment of the present invention comprises at least two sections. The first is an otoscope with an open tip that can be inserted into the ear and manipulated by the user to access the various parts of the ear canal. The second is a base that can be either held in the other hand or set on some folio of surface or support, and preferably provides a display that shows the real-time video image of the user's ear from the point of view of the inserted end of the otoscope. This two section system is small enough to make the entire device portable, while enabling the user to identify and extract material with a high level of precision and safety. The wand and base should either fit comfortably in the palms of the user's hands, or alternatively, the base may be freestanding. When freestanding, the collection chamber can be provided in the base with appropriate tubing connected to the head to facilitate removal of debris by vacuum. For simplicity and ease of use, a hand held device that incorporates the collection chamber in the head is desired. Typically, the size and weight of such a device will be on the same order as conventional otoscopes, as the collection chamber does not need to be very large to accommodate the small amount of wax or other debris that is removed from the patient's ear.

In the preferred embodiments, the otoscope, also referred to as a wand, is configured to have a standard shape as known in the art with a head having an ear speculum with an ear-contacting tip that provides access to the ear canal, and a handle for gripping and manipulating the otoscope, which may be joined together by a narrower neck. See, e.g., http://www.dremed.com/catalog/product_info.php/cPath/61_451_452/products_id/1203—the entire content of which is expressly incorporated herein by reference thereto. In another preferred embodiment, the otoscope has a pistol-shaped body, that can house other components, and an ear speculum with an ear-contacting tip, as well as a pistol grip that can be comfortably held by the user. Alternatively, the otoscope body or housing can be shaped more like a glue- or ray-gun, or miniature hair dryer of course with suction rather than blowing air being provided or removal of ear debris. In another alternate embodiment, the otoscope can have a single uniform body (e.g., oblong like a cell phone, or cylindrical like a cigar or pen) that combines the body and grip portions, and has the ear speculum with ear-contacting tip attached along one of the edges, faces or to the distal end of this combined housing. The otoscope body may also have other shapes and configurations while remaining within the spirit and scope of this invention, as would be recognized by those of ordinary skill in the art.

The best mode contemplated for the present invention has an era speculum with a frusto-conical body and narrower ear-contacting tip with an opening at the distal end. The ear-contacting tip is configured and dimensioned to have an opening at the distal end that can be easily and safely inserted into the outer ear and ear canal. This narrow conical portion or insertion portion preferably has a length that can reach far enough into the ear canal to remove material at the ear drum without posing a hazard to the delicate parts of the ear, and is the insertion portion of the ear-contacting tip. Extra safety can be provided by placing a guard along the narrow conical portion at a point suitable to prevent the insertion portion from being inserted too far into the ear canal. This guard can be a circular disc or stopper. The guard only allows a safe length of the insertion portion of the ear-contacting tip to enter the ear canal to avoid impacting or damaging the ear drum. A disposable or reusable speculum can be placed over the ear-contacting tip up to the guard to protect it from contamination and help prevent the spread of any bacteria or other infectious contaminants between different users.

The tip opening is configured and dimensioned so there is space for a light-providing member, viewing member, and vacuum intake port. The speculum has various-sized openings depending on the size of the patient's ear canal, as well as the opening size desired by the operator. The ear-contacting tip opening is preferably between 3 and 7 mm in diameter, so that it is large enough to contain suitable lenses and allow a full view of the ear canal while providing an opening of appropriate size for suctioning debris from the ear canal.

The cross-sectional area of the opening at the distal end of the ear-contacting tip is separated into three distinct portions including the light providing member, the viewing member and the vacuum intake port. The viewing member has one or more lenses and optical fibers for obtaining an image of the ear canal from a point of view at or near the opening of the ear-contacting tip. The light providing member may have one or more lenses and optical fibers for illuminating the ear canal. The vacuum intake port is an open area at the end of the tip in vacuum communication with the suction source through which debris is evacuated from the ear canal and trapped within the collection chamber of the otoscope.

In the preferred embodiment, the opening is configured and dimensioned such that the vacuum intake port occupies a larger cross sectional area of the opening than the light providing member or the viewing member, and more preferably the vacuum port occupies at least 50% of the opening's cross-sectional area, and most preferably the vacuum port occupies at least 70% of the opening's cross-sectional area at the distal end of the ear-contacting tip. In one embodiment, the light-providing member, vacuum intake port, and viewing member respectively comprise three concentric circles (from largest to smallest) at the opening of the ear-contacting tip. In another embodiment, the light-providing member, vacuum intake port, and viewing member are arrange parallel to the axis of the ear speculum and are adjacent to each other and share the cross-sectional area of the ear-contacting tip opening. In this particular embodiment, the vacuum intake port is preferably located below the viewing member and light providing member to utilize gravity to avoid interference and cross contamination of the viewing member or light providing member. Other configurations and dimensions would be obvious to a person of ordinary skill in the art, while remaining within the scope and intent of the present invention. In another preferred embodiment, the light providing member and viewing member are further back away from the opening at the tip of the ear contacting member, so that 100% of the opening cross-sectional area can be used to suction material and debris out of the ear canal, while still allowing sufficient light to shine through the opening into the ear canal and providing the user a view of the ear canal being suctioned.

The viewing member preferably comprises an image-conveying medium including one or more optical fibers, one or more viewing lenses at the image originating end located at or near the ear-contacting tip opening that can adjust the field of view of the ear canal, and one or more lenses at the terminating end for projecting, focusing and coupling the image from the one or more optical fibers to the image detector. The image detector can be a digital video camera, a charge coupled detector (CCD), or any other solid state image detector having a configuration and dimensions to fit within the otoscope or base, as known in the art. The lens(es) and opening at or sufficiently near the ear-contacting tip of the speculum should provide the largest field of view possible (e.g., 4-7 mm). The camera image can be an actual view, a magnified view (e.g., using a wide-angle or fisheye lens), or an adjustable zoom lens to be controlled on the wand, the base or automatically. The video camera converts the optical image to an electronic signal that can then be sent to and shown on the video display monitor in real time as the ear-contacting tip is moved within the ear canal.

The light providing member preferably comprises a light pipe and a light source, wherein the light pipe can be one or more optical fibers either individually or as a fiber optic bundle, and the light source can be an incandescent bulb, and arc lamp, one or more light-emitting diode (LED), or other photo-luminescent source. A conventional otoscope light source can be used, typically in the form of a 3.5 volt halogen light source. The light providing member can also further comprise any associated lenses and mirrors used to gather and couple the light to the fibers, or direct the light through open space to the opening of the ear-contacting tip, and lens(es) that can focus or spread the light out to illuminate the ear canal at or near the ear-contacting tip opening. The illumination is communicated from the light source to the ear-contacting tip and ear canal by the light providing member components. The light pipe should terminate close to the viewing member, possibly a fiber bundle that fans out or emits light circumferentially about the viewing member or ear-contacting tip opening, so the provided illumination is maximized without interfering with the view or degrading the obtained image. In an alternate embodiment, the light can pass through the open space that coincides with the vacuum intake port. The goal is to allow the user to vacuum the ear canal without interfering with his or her ability to inspect the ear canal (i.e., when the vacuum suctions earwax, it does not or only briefly blocks the lighting or view of the viewing member as debris enters the tip opening).

The suction source can be a fan, blower or vacuum pump operating in a manner that draws air from the ear canal into the ear-contacting tip opening and through the otoscope head that creates a negative pressure or suction to evacuate debris from the ear canal. The fan, blower or pump is driven by a miniature electric motor that can fit within the head or handle, or body or grip depending upon configuration and dimensions of the particular embodiment of the otoscope. The suction source is in vacuum communication with the speculum and opening of the ear-contacting tip through channels molded into the interior portion of the ototscope body, or separate hollow conduits attached to the suction source and vacuum intake port (e.g. flexible tubing).

A collection chamber is located in the head or body of the otoscope, between and in vacuum communication with both the suction source and opening of the ear-contacting tip. The collection chamber is preferably a removable cylindrical or rectangular cartridge, casing or container, although other shapes could be used, having a configuration and dimensions that can be conveniently inserted into a portion of the otoscope body in a manner that places it in vacuum communication with the suction source and vacuum intake port. The chamber is configured and dimensioned to prevent suctioned debris from traversing the distance from the chamber end in vacuum communication with the intake port to the end in vacuum communication with the suction source. This can be accomplished using suitable screens, baffles and/or bends within the collection chamber that prevent debris from reaching or entering the channel or conduit to the suction source to help avoid losing vacuum due to blocking or clogging the suction source, channel or conduit. The otoscope preferably has a door or hatch that can be opened to access the interior portion of the housing, which is configured and dimensioned to contain the removable collection chamber. The interior is accessed for inserting or removing the chamber. The removable cartridge is easily unblocked, cleaned and disinfected by removing it from the otoscope, washing it, and replacing it back in the housing. The removable collection chamber also prevents contamination of other components of the invention. In another embodiment, the collection chamber can be a trap comprising one or more screens, baffles and/or bends that are inserted into the otoscope housing between and in vacuum communication with the intake port and suction source, and can be removed to be cleaned. The collection chamber can also be formed as an integral section of the interior of the otoscope housing, and accessed through the door or hatch, but then debris must be cleaned directly from the otoscope housing. Additional components such as scoops or scrapers can be attached at the opening of the ear-contacting tip to help augment the vacuum extraction of material from the ear by allowing gripping or scrapping of debris from the ear canal walls.

The suction source is in vacuum communication with the collection chamber and the ear-contacting tip of the insertion portion. Vacuum communication between the suction, source, collection chamber and opening can be accomplished with rigid channels formed within the otoscope housing defining a vacuum path between each of the components, or with flexible conduits such as plastic tubing connected to the suction source and one end of the collection chamber, and from the opposite end of the collection chamber to the vacuum intake port. The channel may be formed in the head from the opening to the suction source with the trap or the removable collection chamber interposed between the vacuum intake port and suction source. Placing the suction source as close to the insertion portion as possible minimizes the amount of suction lost by communicating it through a channel or conduit from either the handle portion or base section. In a preferred embodiment, the suction source can have one or more speeds, which can be selected with a switch, or continually adjusted with a control on the wand or alternatively on the base. In another embodiment, the vacuum can be toggled on and off via a gun-like trigger on the wand. The vacuum should also be ventilated to ensure proper air circulation and to maintain an entraining air flow through the ear canal without creating too much of a negative pressure that could cause pain or damage the ear drum.

The display is preferably a compact video display or monitor that is small and light enough to allow the user to hold the base section in one hand while manipulating the otoscope in the other hand. In an alternate embodiment, the display can be a full flat screen monitor that can be placed on a table or support, but still be portable. The display can present the images obtained by the digital video camera or other image detector.

The power source can be a transformer that is connected to an electrical outlet, or batteries that can be replaceable or rechargeable. This would allow the device to be cordless or cord-operated. The power supply is operatively connected so as to provide electricity to the other components of the invention including the suction source, light source, image detector, and video display by wire(s) or electrical cable(s).

The controls can be any combination of switches, dials, slides pressure pads or the like known in the art for controlling the operation of such components described above.

Each of the components can be located in either the otoscope head or handle, or in the base, or in any combination thereof without diverging from the spirit and scope of the invention.

In the preferred embodiment, the image detector, optics, lens(es), light source, fiber optics, suction source and collection chamber are all contained in the otoscope, and the video display and power source are located in the base. By locating the light providing member in the wand, the size of the light source and the voltage needed to provide sufficient light is minimized, and the length of optical fiber is reduced. By locating the suction source in the wand, the size of the fan and the power needed to create the necessary suction (or the need for a hose to the base) is minimized. Locating the video display and power source within the base ensures the most overall compact, easy-to-hold construction of the wand.

In the preferred embodiment, the handle of the otoscope is preferably of an annular shape and configured and dimensioned to house the suction source, a light source, and the optics and electronics of a miniature digital video camera. The head preferably houses the viewing optics and light providing optics, plus the fiber optics that provide illumination and image communication with the light source and video camera. The otoscope head also preferably houses a collection chamber for capturing any extracted material before it can block or clog the vacuum conduit or channel in vacuum communication with the suction source.

The vacuum intake port, collection chamber, viewing member, and light providing member can be arranged within the otoscope in a such a manner that the intake port, light providing member and viewing member are all aligned concentrically along the axis of the ear-contacting tip. Alternately, the vacuum intake port, viewing member, and light providing member can be arranged adjacent to each other in a parallel manner along the axis of the ear-contacting tip. In either embodiment, the vacuum intake port occupies a larger cross sectional area of the opening than the light providing member or the viewing member, and more preferably the vacuum port occupies at least 50% of the opening's cross-sectional area, and most preferably the vacuum port occupies at least 70% of the opening's cross-sectional area at the distal end of the ear-contacting tip. Preferably, the vacuum intake port is located below the viewing member and light providing member to work with gravity to suction debris while avoiding blocking the viewing member or light providing member.

Interference or cross-contamination between the video camera and optics, light source and suction source can be avoided by providing separate components arranged in the parallel manner rather than in the concentric arrangement, since the viewing member and light providing member are separated from the vacuum intake port. Debris being suctioned out of the ear canal, therefore, does not have to pass by the viewing member and light providing member to enter the vacuum port.

The handle of the otoscope can alternately be configured and dimensioned to contain batteries to power the components within the head portion. This also allows for a wireless construction. In an alternate embodiment, the components can be housed in both the head and handle of the otoscope body, and a power cord can connect the otoscope to a power source in the base section or an external power source plugged into a standard wall outlet to provide power to the electrical components. Removing the batteries and connecting the otoscope to the base section with a power cord minimizes the weight and clumsiness of the otoscope. The power cord or cable is preferably attached to the bottom of the otoscope handle, although in some embodiments it may be attached directly to the head or elsewhere on the otoscope body.

In alternative embodiments, the suction source, the video camera, optics, lens(es), light source, video display, power source and/or other components can be located in the base, and connect to the wand via one or more cables containing any necessary wires, hoses, tubing, conduits and/or optical fibers or bundles. Locating these components in the base, as opposed to the wand, can help minimize the size and weight of the wand.

The vacuum collection chamber or trap, however, should always be located in the wand to avoid clogging any vacuum conduit or tubes. The components of the wand—e.g., the vacuum collection chamber or trap, ear contacting tip, light pipe and lens(es), fiber optics and/or viewing lens(es) are preferably easy to clean/unblock clogs, and disinfect. The collection chamber is also preferably removable. The device can also include interchangeable speculums that snap on or mount on to the end of the wand as are commonly used in conventional otoscopes.

To avoid causing any damage to the ear, ear canal, or eardrum, a prophylactic or safety device—e.g., a plastic stopper or ear guard—can be close to the end of the ear-contacting tip of the insertion portion of the ear speculum to limit the depth to which the device can be inserted.

In another alternate embodiment, the suction source, light source, video camera, display and power supply can all be contained within the base section, and the otoscope would then contain only the collection chamber. The base section is connected to the otoscope by one or more cable(s) that contains all the necessary electrical wires, fiber optics, tubing and conduits. The otoscope can then be configured in the shape of a pen or cylinder for this alternate embodiment, since there is no need to house the components that are located in the base section. This make the otoscope much easier to manipulate by the user The suction source can then be in vacuum communication with the otoscope and collection chamber by a flexible conduit, such rubber or plastic tubing. The flexible conduit is connected to and in vacuum communication preferably with the proximal end of the collection chamber, which is in vacuum communication with the opening of the ear contacting tip of the otoscope. The hand held design enables suction air flow at under 70 decibels and the provision of the suction source in the base provides even lower values.

The light source is in illumination communication with the ear-contacting tip by a light pipe that can comprise one or more optical fibers in a bundle for transmitting the light from the base to the otoscope, and lens(es) for coupling the light from the illumination source to the optical fibers, as well as other components such as reflectors for improving the illumination provided by the light source in the base to the light pipe. The tip(s) of the optical fiber(s) can be hemispherical to act as a lens to cause the light beam to diverge and spread out to illuminate a larger portion of the ear canal in a more uniform manner. Alternatively, actual lens(es) can be placed at the end of the optical fiber(s) to spread the light from the fibers out more uniformly.

The video camera located in the base can also be in light and image communication with the hand-held portion using a separate optical fiber to transmit the observed image from the otoscope back to the video camera in the base section. Any optics necessary to focus and/or improve the image and couple it to the optical fiber(s) are in the otoscope. The optics in the otoscope can provide the actual view, a wide-angle view or a magnified view of the ear canal preferably with an adjustable zoom lens that can be controlled by the user. The particular lens and opening at the tip of the insertion section, as well as the positioning of the lens within the otoscope preferably provides the largest field of view possible (e.g., 4-7 mm). The optics may also be adjusted automatically as is known in conventional otoscopes. The image is communicated by fiber optics to the lens(es) within the base, which project, focus and couple the image onto the image detector. The image detector converts the image to electrical signals that can be shown on the display. The display can either be housed within the base, or be a separate portable monitor that is functionally associated with or plugs into the base.

The method of use comprises the user placing the insertion portion of the ear speculum at the edge of the ear or partially inside the ear canal to allow the lighting means to illuminate the ear canal and imaging means to obtain a real time image and broadcast or output the signal to a video display, so one can examine the inside of their own ear canal. The user can then switch on the suction source at a particular speed, manipulating the device to adjust the angle of the wand, and safely and precisely identify and simultaneously suction out the earwax and other contaminants while viewing the operation and results on a display. Collection of the suctioned debris is done by a trap or collection chamber located in the wand. A user can extract debris from his or her own an ear canal by being provided with one of the described otoscopes, inserting the ear-contacting tip into a user's ear canal, observing the interior of the his own ear canal on a display, turning on a suction source to generate a vacuum, vacuum debris from the ear canal while actively viewing the ear canal on the display; and trapping debris vacuumed from the user's ear canal.

The following explanations of the figures discuss examples of the preferred embodiments and are not meant to limit the scope of the invention.

Figure 1:
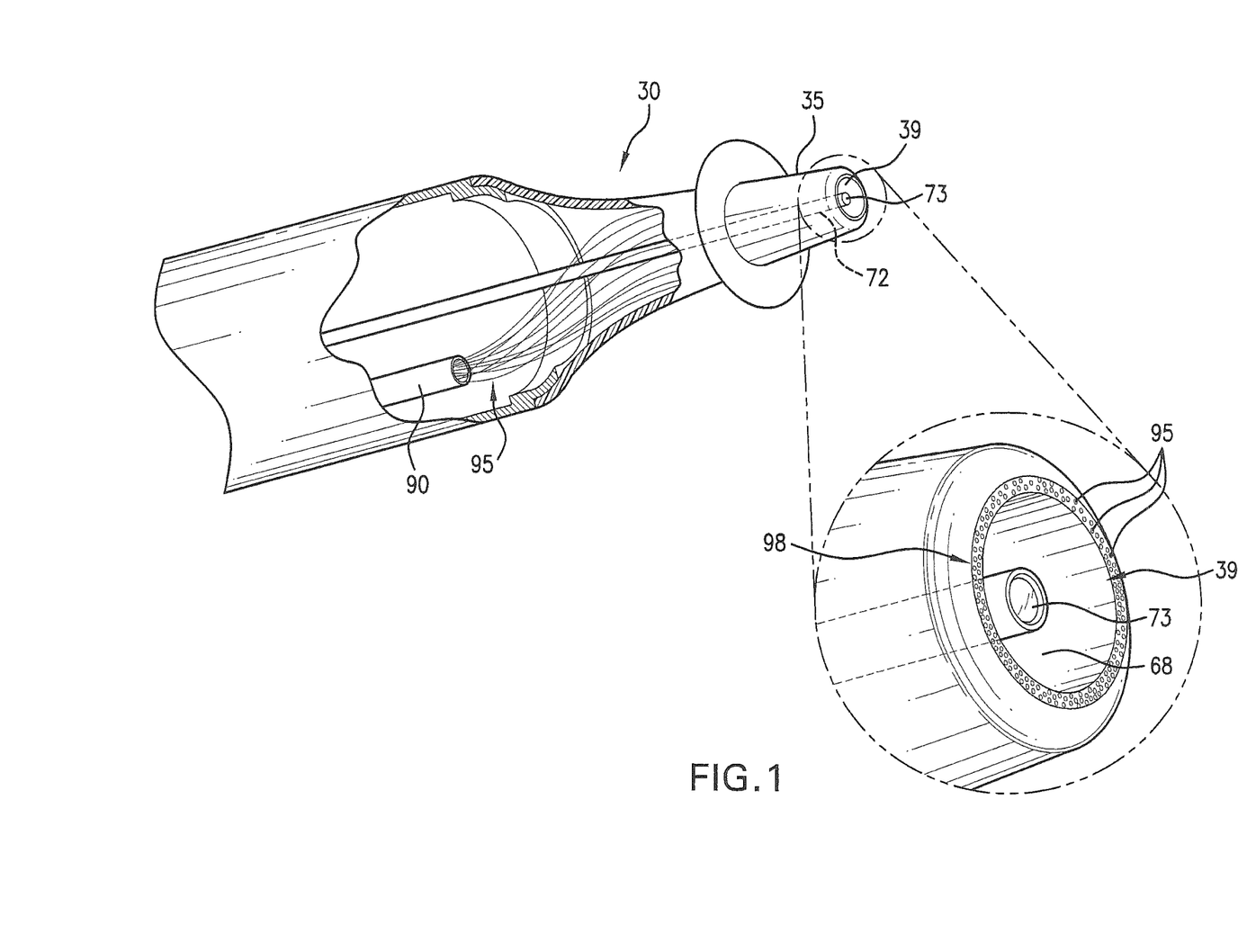
FIG. 1 is a cross-sectional view of an embodiment of an ear speculum of the present invention.

FIG. 1 depicts a preferred embodiment of the ear speculum 30, for any of the otoscopes described above, having an ear-contacting tip 35 and opening 39 at the distal end of the ear-contacting tip 35 having a diameter and cross-sectional area. A plurality of optical fibers 95 fan out from a fiber optic bundle 90 to form an outer circumferential light ring 98 around the peripheral edge of the opening 39 in the ear-contacting tip 35. An image obtaining lens 73, which can be a wide angle or zoom lens, is shown centered within the opening 39 of the ear-contacting tip 35. A vacuum intake port 68 occupies the space of the opening 39 between the lens 73 and the light ring 98. The vacuum intake port occupies a larger cross sectional area of the opening 39 than the light ring 98 or the viewing member optics 72, and more preferably the vacuum port occupies at least 50% of the opening's cross-sectional area, and most preferably the vacuum port occupies at least 70% of the opening's cross-sectional area. The lens 73 and optics 72 may be further back away from the opening 39 at the tip of the ear contacting member 35, so that between 70% and 100% of the opening cross-sectional area can be used to suction material and debris out of the ear canal, while still allowing sufficient light to shine through the opening 39 into the ear canal and providing the lens 73 and optics 72 a sufficient view of the ear canal being suctioned.

Figure 2:
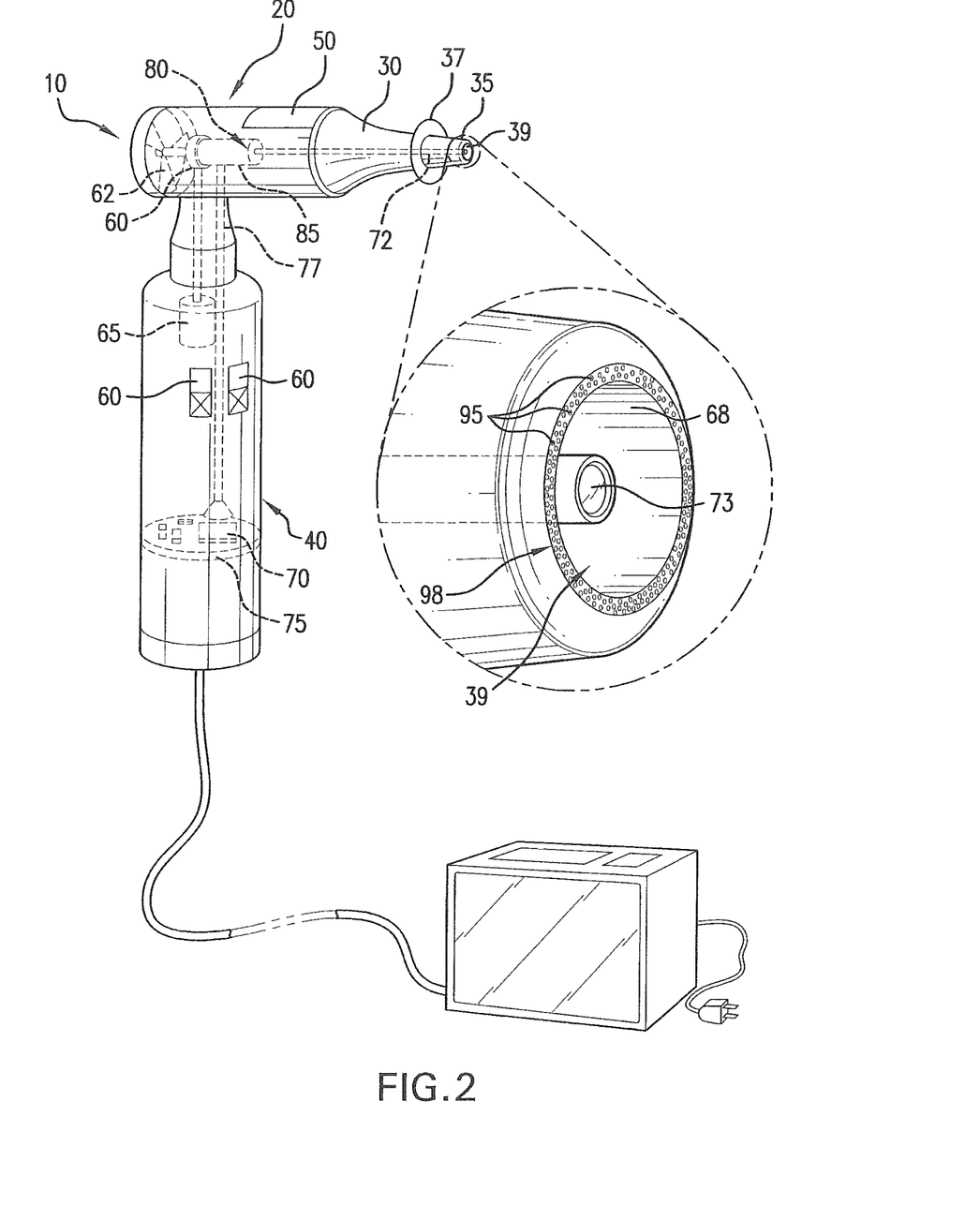
FIG. 2 is a perspective view of a first preferred embodiment of the present invention.

FIG. 2 depicts a preferred embodiment having an otoscope 10 with an ear speculum 30 having an ear-contacting tip 35 at one end of the head 20, and a disc shaped guard 37 positioned along the length of and perpendicular to the narrow tapered end of the ear-contacting tip 35. A removable collection chamber 50 is positioned adjacent to and in vacuum communication with the ear-contacting tip 35. A fan or blower 62 of the suction source 60 is located at the end of the head 20 opposite the ear speculum 30, and in vacuum communication with the removable collection chamber 50 and ear-contacting tip 35. The suction source 60 is in vacuum communication with the removable collection chamber 50 and the opening 39 at the distal end of the ear-contacting tip 35. The fan or blower 62 generates sufficient suction to extract material from the ear canal, through the opening 39 in the ear-contacting tip 35, which is then trapped within the collection chamber 50. The user holds the otoscope 10 by the handle 40. In this particular embodiment, the handle houses the motor 65 for the suction source 60 that drives the blower or fan 62. The electronics 75 for the miniature video camera 70 can also be housed within the handle 40 of the otoscope 10. The video camera is in image communication with the optics 72 located within the ear-contacting tip 35 by a suitable optical fiber 77. The optics 72 can include a wide angle or zoom lens 73 positioned concentrically at the opening 39 of the ear-contacting tip 35. A light providing member 80 with a light source 85 can be located in the head 20 or handle 40 of the otoscope 10, and in light communication with the opening 39 at the end of the ear contacting tip 35. The light can be communicated to the opening 39 by a plurality of optical fibers 95 in a fiber optic bundle 90 that fans out to form a ring 98 around the peripheral edge of the opening 25 in the ear-contacting tip 20, and are concentric with the optics 72 and vacuum intake port 68. Controls for the suction source 60, light source, and camera optics 72 such as switches, slides or dials, can be located on the handle or head of the otoscope.

Figure 3:
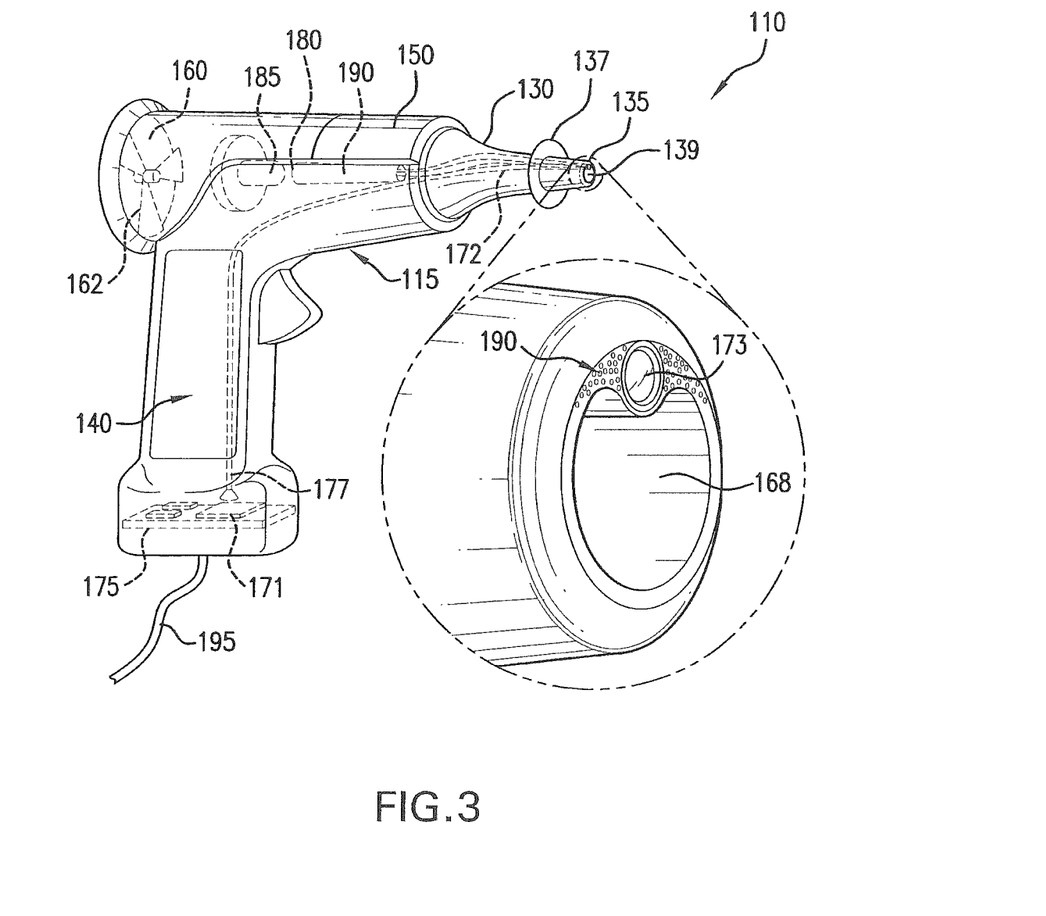
FIG. 3 is a perspective view of second preferred embodiment of the present invention.

FIG. 3 depicts a preferred embodiment having a pistol-shaped otoscope 110 with an ear speculum 130 at one end of the pistol body 115, and a disc shaped guard 137 positioned along the length of and perpendicular to the narrow tapered end of the ear-contacting tip 135 of the ear speculum 130. A removable collection chamber 150 is positioned within the pistol body 115, adjacent to and in vacuum communication with the ear-contacting tip 135. The suction source 160 is in vacuum communication with the removable collection chamber 150 and the opening 139 at the distal end of the ear-contacting tip 135. The fan or blower 162 generates sufficient suction to extract material from the ear canal, through the vacuum intake port 168 in the ear-contacting tip 135, which is then trapped within the collection chamber 150. The user holds the otoscope 110 by the pistol grip 140. In this particular embodiment, the handle houses the motor 165 for the suction source 160 that drives the blower or fan 162. The electronics 175 for the miniature video camera 171 can be housed within the pistol grip 140 or body 115 of the otoscope 110. The video camera 171 is in image communication with the optics 172 located within the ear-contacting tip 120 by a suitable optical fiber 177. The optics 172 can include a wide angle or zoom lens 173 positioned adjacent to and parallel with the fiber optic bundle 190 at the opening 139 of the ear-contacting tip 135.

A light source 185 for the light providing member 180 can be located in the pistol body 115 or grip 140 of the otoscope 110, and in light communication with the opening 139 at the end of the ear contacting tip 135. The light can be communicated to the opening 139 by a plurality of optical fibers 195 in a fiber optic bundle 190 that branches into two separate bundles 192 adjacent to and on either side of the optics 172 at the opening 125 in the ear-contacting tip 135, and above the vacuum intake port 168. The vacuum intake port occupies a larger portion of the cross-sectional area of the ear-contacting tip opening 139 than the light providing member or viewing member, and can preferably be at least 50% of the area, and more preferably at least 70% of the area. Controls for the suction source 160, light source 185, and camera optics 172 such as switches, slides or dials, can be located on the pistol grip 140 or body 115 of the otoscope 110. A cord or cable 195 is attached to the bottom of the pistol grip 140 to supply power to the suction source motor 165 and transmit the image obtained by the viewing member 170 to the display 199.

Figure 4:
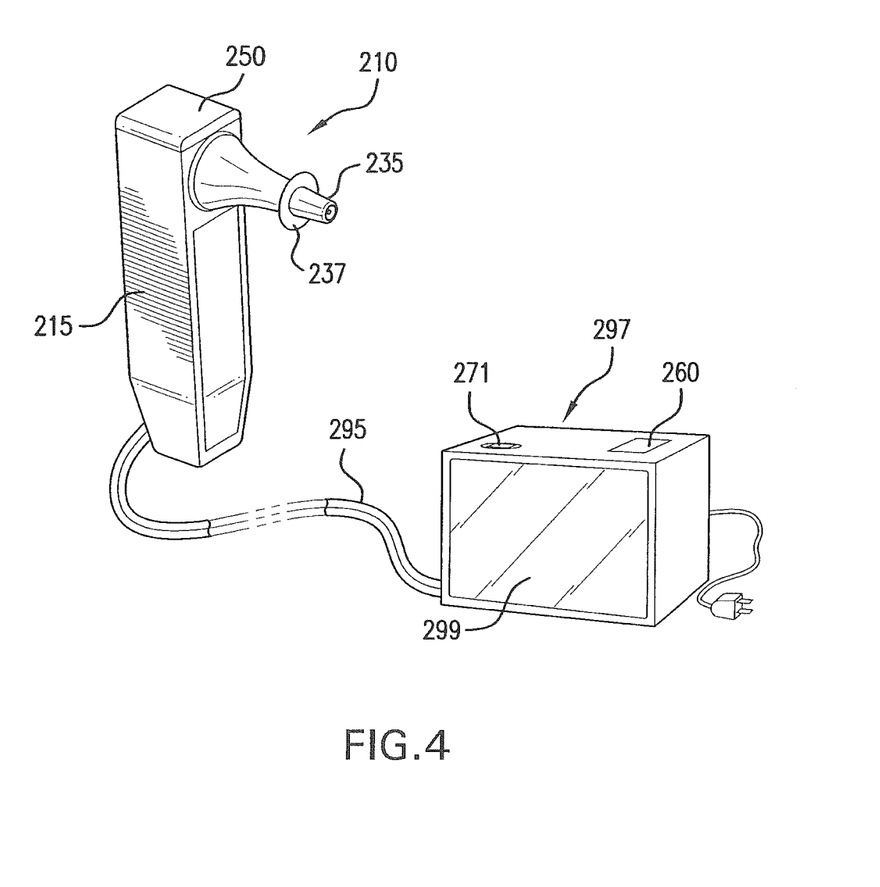
FIG. 4 is a perspective view of a third preferred embodiment of the present invention.

FIG. 4 depicts a preferred embodiment combining the handle and head into a single uniformly shaped otoscope body 215 with a rectangular cross-section. The ear contacting tip 235 is located on one face of the rectangular body, and has a disc shaped guard 237 positioned along the length of and perpendicular to the narrow tapered end of the insertion portion of the ear-contacting tip 235. FIG. 3 shows the suction source 260 and video display monitor 299 located in the base 297 and connected to the otoscope 215 by a cable 295 having a flexible tube for vacuum communication and electrical wiring to supply power and transfer electronic signals between the otoscope 210 and the base 297. The optics and electronics for the video camera 271 are located in the body 215. The collection chamber 250 is accessed by either removing it from the body or opening a door in the body 215.

In an alternative embodiment, the device may be powered by batteries and be rechargeable. It may also include the appropriate computer chip for programming use to regulate lighting, vacuum level, collection chamber fill, etc. Battery life can provide portable power for multiple uses before recharging is necessary. An LED power level light can be provided for this embodiment.

It should be noted that the use of the singular should be interpreted to include the plural, and the plural to include the singular in describing the components of the invention.

While specific examples and embodiments have been described, any combination of the components may be located within the otoscope or the base, and within either the head or body of the otoscope without deviating from the spirit and scope of the present invention, as would be recognized by a person of ordinary skill in the art. Any such combination or arrangement of components should be considered to fall within the scope of the present invention.

What is claimed is:

1. An ear speculum comprising:
   a body having an ear-contacting tip with an opening;
   a light providing member;
   a viewing member; and
   a vacuum intake port,
   wherein the light providing member, viewing member and vacuum intake port extend within and through the ear-contacting tip and the ear-contacting tip opening is configured and dimensioned with a cross-sectional area that provides sufficient space therein for the light providing and viewing members and the intake port, the light providing member provided in a ring that at least partially extends around a peripheral edge of the ear-contacting tip opening, and with the vacuum intake port occupying at least 50% of the cross-sectional area of the ear-contacting tip opening to facilitate removal of material from an ear canal.

2. The ear speculum of claim 1, wherein:
   the light providing member comprises optical fibers; and
   the viewing member comprises a lens.

3. An otoscope comprising:
   a head;
   an ear speculum of claim 1 in operative association with the head;
   an image detector in image communication with the viewing member;
   a suction source in vacuum communication with the vacuum intake port; and
   a light source in illumination communication with the light providing member.

4. The otoscope of claim 3, which further comprises:
   a collection chamber in vacuum communication with both the suction source and vacuum intake port, wherein the vacuum intake port is in vacuum communication with the suction source through the collection chamber.

5. The otoscope of claim 4, wherein the head is configured and dimensioned to house the suction source and collection chamber.

6. The otoscope of claim 4, wherein the collection chamber is configured and dimensioned such that material suctioned through the vacuum intake port from an ear becomes trapped within the collection chamber before reaching the vacuum source.

7. The otoscope of claim 3, which further comprises:
   a display for presenting an image obtained by the viewing member;
   optical components for adjusting the image obtained by the viewing member; and
   a power source operatively connected to the suction source, light source, image detector and display.

8. The otoscope of claim 7, which further comprises controls for adjusting the suction source, light source, optical components and display.

9. The otoscope of claim 7, which further comprises a base in communication with the head, wherein the base is configured and dimensioned to house the suction source, the display and the power source, and the suction source is in vacuum communication with the vacuum intake port through a collection chamber located in the speculum.

10. The otoscope of claim 7, wherein the optical components include a wide angle lens or a zoom lens.

11. The otoscope of claim 3, wherein the viewing member and light providing member are arranged adjacent each other within a ring that extends around the peripheral edge of the ear-contacting tip.

12. The otoscope of claim 3, wherein the light providing member includes optical fibers that are arranged concentrically within the ring that extends around the peripheral edge of the ear-contacting tip opening, the vacuum port occupies at least 70% of the cross-sectional area of the ear-contacting tip opening, and the viewing member is positioned at the center of the ear-contacting tip opening.

13. A system for removing material from an ear canal, comprising:
   an otoscope having a head;
   an ear speculum having a proximal end in operative association with the head, and a distal end having an ear-contacting tip having a distal opening;
   a vacuum intake port within the ear-contacting tip;
   a suction source in vacuum communication with the vacuum intake port, wherein the suction is sufficient to remove any observed material from the ear canal;
   a light providing member within the ear-contacting tip;
   a viewing member within the ear-contacting tip;
   a collection chamber in vacuum communication with both the suction source and vacuum intake port, wherein the vacuum intake port is in vacuum communication with the suction source through the collection chamber;
   a light source in illumination communication with the light providing member;
   optics that can obtain and transfer an image of the ear canal to a camera;
   a base in communication with the otoscope;
   a display within the base that presents the image obtained by the camera;
   a power source within the base electrically connected to the suction source, light source and display; and,
   controls for adjusting the suction, illumination and display,
   wherein the light providing member, viewing member and vacuum intake port extend within and through the ear-contacting tip and the ear-contacting tip opening is configured and dimensioned with a cross-sectional area that provides sufficient space therein for the light providing and viewing members and the intake port, the light providing member provided in a ring that at least partially extends around a peripheral edge of the ear-contacting tip opening, and with the vacuum intake port occupying at least 50% of the cross-sectional area of the ear-contacting tip opening to facilitate removal of material from an ear canal into the collection chamber.

14. An ear-wax removal device comprising:
a body having an ear-contacting tip with an opening;
a light providing member;
a viewing member; and
a vacuum intake port provided within the ear-contacting tip opening and occupying at least 50% of a cross-sectional area of the ear-contacting tip opening;
wherein the light providing member, viewing member and vacuum intake port extend within and through the ear-contacting tip and the ear-contacting tip opening is configured and dimensioned with a cross-sectional area that provides sufficient space therein for the light providing and viewing members and the vacuum intake port;
the light providing member provided in a ring that at least partially extends around a peripheral edge of the ear-contacting tip opening; and
wherein the body is a pistol-shaped body having pistol grip that can be comfortably held by an operator of the device.

15. The device of claim 14 further comprising
a suction source in vacuum communication with the vacuum intake port.

16. A system for removing material from an ear canal, comprising:
an otoscope having a head;
an ear speculum comprising a body having an ear-contacting tip that includes a proximal end in operative association with the otoscope head and a distal end having an opening;
a vacuum intake port within the ear-contacting tip;
a suction source in vacuum communication with the vacuum intake port, wherein the suction is sufficient to remove any observed material from the ear canal;
a light providing member within the ear-contacting tip;
a viewing member within the ear-contacting tip;
a collection chamber in vacuum communication with both the suction source and vacuum intake port, wherein the vacuum intake port is in vacuum communication with the suction source through the collection chamber;
a light source in illumination communication with the light providing member;
optics that can obtain and transfer an image of the ear canal to a camera;
a base in communication with the otoscope;
a display for receiving and presenting the image obtained by the camera; and
controls for adjusting the suction and illumination,
wherein the light providing member, viewing member and vacuum intake port extend within and through the ear-contacting tip and the ear-contacting tip opening is configured and dimensioned with a cross-sectional area that provides sufficient space therein for the light providing member, the viewing member and the vacuum intake port, the light providing member provided in a ring that at least partially extends around a peripheral edge of the ear-contacting tip opening,
wherein the light providing member comprises a plurality of fiber optic components; and
wherein the vacuum port occupies at least 70% of the cross-sectional area of the ear-contacting tip opening.

* * * * *